United States Patent
Amano et al.

(10) Patent No.: US 7,024,367 B2
(45) Date of Patent: Apr. 4, 2006

(54) BIOMETRIC MEASURING SYSTEM WITH DETACHABLE ANNOUNCEMENT DEVICE

(75) Inventors: Yoshinori Amano, Ehime (JP); Yoshinobu Tokuno, Ehime (JP); Yoshihiro Kataoka, Ehime (JP); Yoshiharu Sato, Kyoto (JP); Shoji Kawanaka, Kyoto (JP)

(73) Assignees: Matsushita Electric Industrial Co., Ltd., Osaka (JP); Arkray, Inc., Kyoto (JP)

( * ) Notice: Subject to any disclaimer, the term of this patent is extended or adjusted under 35 U.S.C. 154(b) by 616 days.

(21) Appl. No.: 09/958,990

(22) PCT Filed: Feb. 19, 2001

(86) PCT No.: PCT/JP01/01150

§ 371 (c)(1),
(2), (4) Date: Dec. 12, 2001

(87) PCT Pub. No.: WO01/61340

PCT Pub. Date: Aug. 23, 2001

(65) Prior Publication Data

US 2002/0138275 A1    Sep. 26, 2002

(30) Foreign Application Priority Data

Feb. 18, 2000  (JP) .............................. 2000-041713

(51) Int. Cl.
*G10L 21/00*  (2006.01)

(52) U.S. Cl. ...................... 704/272; 704/270; 704/274; 704/258; 704/275; 600/483; 600/485; 600/549; 340/321; 340/573.1; 705/3

(58) Field of Classification Search ................ 704/270, 704/258, 272, 274; 600/483, 485, 549; 340/321, 340/573.1; D10/57; 705/3
See application file for complete search history.

(56) References Cited

U.S. PATENT DOCUMENTS

| | | | | |
|---|---|---|---|---|
| 4,428,685 A | * | 1/1984 | Lemelson et al. | 600/549 |
| 4,810,996 A | * | 3/1989 | Glen et al. | 340/573.1 |
| 4,998,534 A | * | 3/1991 | Claxton et al. | 600/483 |
| 5,594,638 A | * | 1/1997 | Iliff | 705/3 |
| D379,936 S | * | 6/1997 | Wei-Hsin | D10/57 |
| 6,537,214 B1 | * | 3/2003 | Hood et al. | 340/573.1 |

FOREIGN PATENT DOCUMENTS

| | | | |
|---|---|---|---|
| CA | CN 1282073 | * | 4/2000 |
| DE | 29901739 U | * | 9/1999 |
| EP | 0160534 | | 11/1985 |
| FR | 2 664 615 | * | 3/1989 |
| FR | 2 756 630 | * | 12/1997 |
| JP | 55-150066 | * | 5/1979 |

(Continued)

*Primary Examiner*—Vijay Chawan
(74) *Attorney, Agent, or Firm*—Wenderoth, Lind & Ponack, L.L.P.

(57) ABSTRACT

A measuring system according to the present invention includes a biosensor 2, and a measuring device 1 capable of assaying a specified component in a biological sample applied to the sensor 2. An announcement device 22 indicates a measuring procedure or a measurement result in the measuring device 1 by voice or the like by being combined with the measuring device 1.

28 Claims, 7 Drawing Sheets

FOREIGN PATENT DOCUMENTS

| | | | |
|---|---|---|---|
| JP | 62-046238 | * | 8/1985 |
| JP | 61-194504 | | 12/1986 |
| JP | 62-46238 | | 2/1987 |
| JP | 06-142061 | * | 5/1994 |
| JP | 9-94231 | | 4/1997 |
| JP | 09-094231 | * | 4/1997 |

* cited by examiner

Fig.6 PRIOR ART
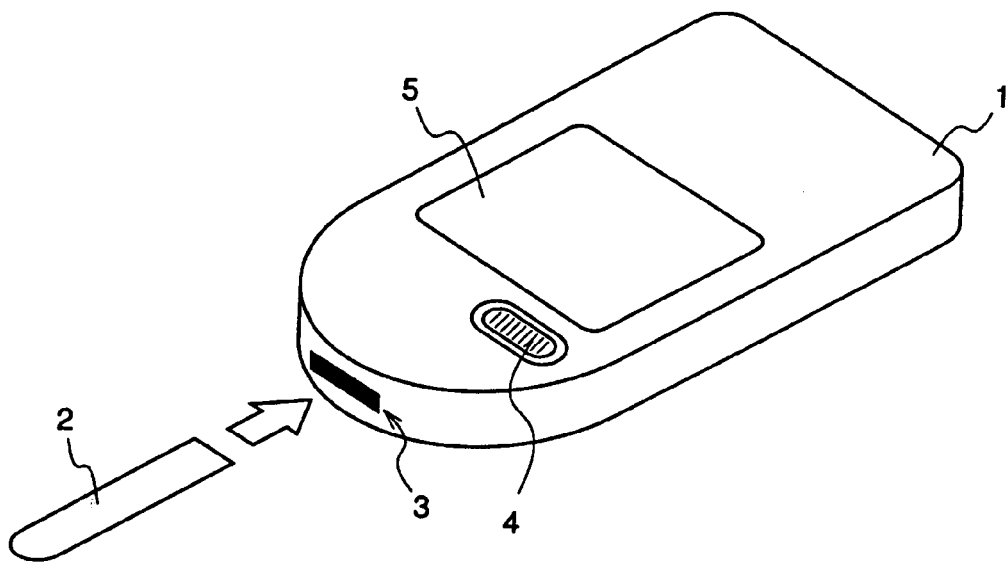
Fig.7 PRIOR ART
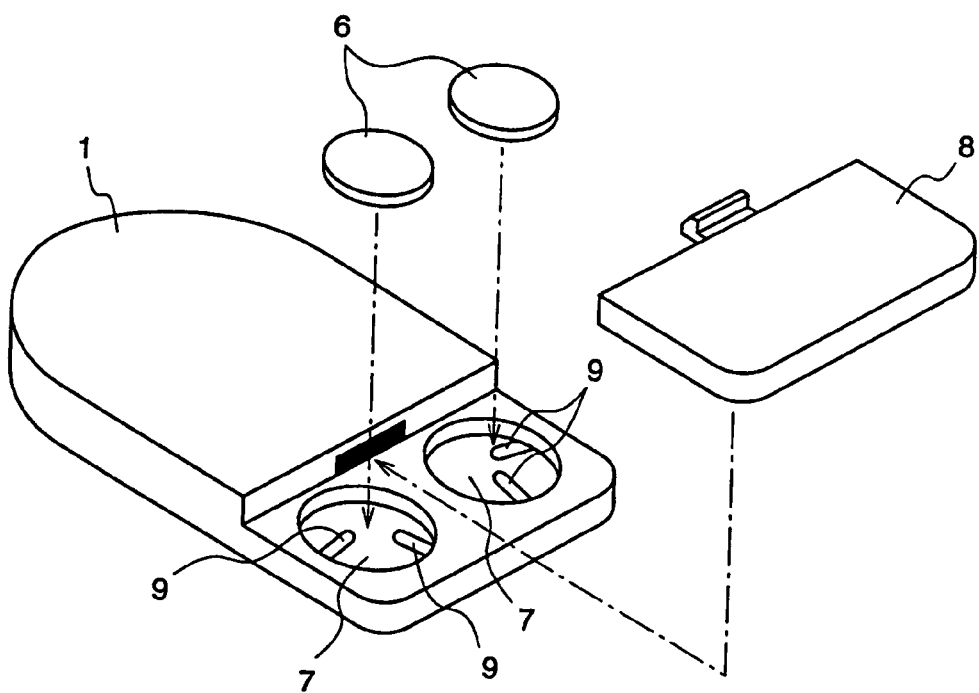

BIOMETRIC MEASURING SYSTEM WITH DETACHABLE ANNOUNCEMENT DEVICE

TECHNICAL FIELD

The present invention relates to a measuring system which comprises a biosensor measuring device suitable for a biosensor that can accurately, speedily, and easily assay a specific component in various biological samples, and an optional device that can be combined with the measuring device and complementarily announces a measuring procedure and a measurement result in the measuring device by voice.

BACKGROUND ART

An example of a biosensor measuring device employing a biosensor will be illustrated in FIGS. 6 and 7. A measuring device 1 is provided with a sensor insertion slot 3 in which a biosensor 2 is inserted, an operation button 4 for performing various operations, and a display means 5 for displaying various kinds of information such as a measurement result and time. A storage part 7 for a battery 6 is provided on the reverse face, and the battery 6 is fixed in a state in which the battery 6 is pushed to a contact point 9 by a back cover 8. Inside the measuring device 1, a measuring part comprising a converting means for converting an electrical resistance value of the liquid to be examined (sample) obtained by the biosensor 2 to a characteristic value (such as a blood sugar level) of the liquid to be examined, a storage means for the characteristic value, and a calculating means for performing various arithmetical operations such as an average value calculation based on a value stored in the storage means or the characteristic value obtained by measurement, a control means of the display means 5, and the like are provided by being formed on a printed board (not shown).

The biosensor 2 is provided with a counter electrode 11 and a measuring electrode 12, leads 13 and 14 connected thereto, and an insulating layer 15 on the surface of a substrate 10 as shown in FIG. 8. A reactive layer (not shown) including enzyme and a mediator (electron acceptor) is formed so as to cover the counter electrode 11 and the measuring electrode 12. The surface of the substrate 10 is sequentially covered with a spacer 17 which has a U-shaped notch part 16 at a section corresponding to the measuring electrode 12, and a cover 19 has an air vent 18 communicating with the notch part 16 of the spacer 17. The substrate 10, the spacer 17, and the cover 19 are attached to one another, thereby constructing the biosensor 2. Numeral 20 denotes an attaching end to be attached to the measuring device 1, and numeral 20a denotes a projection part for preventing an inverse insertion of the biosensor 2 to the measuring device 1. Therefore, in a state in which the attaching end 20 of the biosensor 2 is attached to the measuring device 1, when liquid to be examined (sample) drops to the end of the biosensor 2, the liquid to be examined is led onto the counter electrode 11 and the measuring electrode 12 through the notch part 16 by capillary action, and the air on the counter electrode 11 and the measuring electrode 12 is discharged from the air vent 18.

After measurement, the characteristic value obtained by the converting means of the measuring device 1 is displayed on the display means 5.

The output of the measurement result is performed only by a display by the display means 5 in the biosensor measuring device 1 of the above-described construction. However, when a user is a weak-sighted person, for example, it is difficult to confirm the display.

A measuring device as shown in FIG. 9 is invented as a countermeasure for the problem. In FIG. 9, the same reference numerals as those shown in FIG. 6 denote the same components. A voice output part 21 is provided on the surface of the measuring device 1 in addition to the display means 5, and a voice output means for announcing a characteristic value or various kinds of information by voice is provided inside the measuring device 1, besides the measuring part (both of them not shown).

However, in the above-described construction, the measuring device becomes expensive because all the parts from measurement to voice output are built in the measuring device. When plural users require the voice output, for example, each person is required to have the expensive device. Further, when the voice output part has a breakdown, the whole device has to be repaired and exchanged, resulting in inconvenience for a user.

SUMMARY OF THE INVENTION

The present invention is made to solve the above-mentioned problem. Its object is to provide a measuring system which comprises a measuring device capable of receiving a substance to be measured, analyzing components of the substance to be measured, and displaying a measured value and an optional (announcement) device having a voice output part. The system can complementarily announce a measurement result and a measuring procedure in the measuring device by voice from the announcement device to a user by combining the measuring device with the announcement device.

According to a first aspect of the present invention, a measuring system includes a measuring device which receives a substance to be measured, analyzes a component of the substance to be measured, and displays its measurement result. An optional device (announcement device) has a voice output means for generating a voice or the like by being combined with the measuring device, and the announcement device complementarily announces a measuring procedure or a measurement result in the measuring device by voice. Therefore, even a weak-sighted person or those unfamiliar with handling of the device can perform measurements accurately and be informed of the measurement results. Further, the measuring device and the announcement device can be constructed to be integrated and separated, so that it is possible to deal with weak-sighted people and others respectively. Thus, even when plural users require a voice function, only the measuring device which manages measurement data has to be held by each person and the announcement device can be shared, resulting in reduction of the user's burden. Further, when a voice output part has a breakdown, only the announcement device has to be repaired and exchanged, and the measuring device can be used continuously, thereby enhancing convenience for a user.

According to a second aspect of the present invention, in the measuring system of the first aspect, the measuring device has a means for establishing communication of information about measurement with the announcement device. Therefore, it is possible to transfer data such as a measurement results from the measuring device to the announcement device.

According to a third aspect of the present invention, in the measuring system of the first aspect, the announcement device has a means for establishing communication of information about measurement with the measuring device. Therefore, the announcement device can receive data such as a measurement result transferred from the measuring device.

According to a fourth aspect of the present invention, in the measuring system of the first aspect, an operating part for operating the voice output means is arranged on the side of the announcement device. Therefore, when an operator holds the system, the operation is easily performed, and operates well.

According to a fifth aspect of the present invention, in the measuring system of the first aspect, the announcement device has a function for switching the language of the voice. Therefore, it is possible to cope with a wide range of languages according to a user.

According to a sixth aspect of the present invention, in the measuring system of the first aspect, an operating lever for switching a language of a voice is arranged so as to be covered up with an exterior case of the announcement device. Therefore, a user can be prevented from accidentally switching a voice language.

According to a seventh aspect of the present invention, in the measuring system of the first aspect, a slope with a tapered shape is provided in the neighborhood of an opening for the measuring device to be inserted. The opening is provided in the announcement device, and the tapered shape slopes in the direction where the measuring device is inserted. Therefore, the slope provided in the announcement device serves as a guide, thereby enabling a reliable integration of the measuring device and the announcement device.

According to an eighth aspect of the present invention, in the measuring system of the first aspect, the measuring device and the announcement device have mechanisms for engaging each other when being combined. Therefore, it is possible to realize a simple integration and a strong fixation of the measuring device and the announcement device.

According to a ninth aspect of the present invention, in the measuring system of the first aspect, an operating part for releasing a combination of the measuring device and the announcement device is provided on the base side of the announcement device. Therefore, the operating part can be prevented from unexpectedly operating to release a combination of the measuring device and the announcement device.

According to a tenth aspect of the present invention, in the measuring system of the first aspect, on the base side of the measuring device, there is provided a concave portion which is locked with a locking means on the announcement device side when combined with the announcement device. Therefore, a combination of the measuring device and the announcement device can be released by a simple operation.

According to an eleventh aspect of the present invention, in the measuring system of the first aspect, the measuring device can be inserted into the announcement device only from one direction of the measuring device when the measuring device and the announcement device are combined with each other. Therefore, the measuring device can be prevented from wrongly being inserted into the announcement device, thereby preventing breakage of both devices.

According to a twelfth aspect of the present invention, in the measuring system of the first aspect, the measuring device and the announcement device are provided with mechanisms for preventing a wrong insertion of the measuring device into the announcement device. Therefore, the measuring device can be prevented from being wrongly inserted into the announcement device, thereby preventing breakage of both devices.

According to a thirteenth aspect of the present invention, in the measuring system of the first aspect, a rib for regulating the distance to the measuring device is provided on the inner wall of the announcement device. Therefore, the measuring device can be prevented from being excessively inserted in the announcement device, thereby preventing breakage of both devices.

According to a fourteenth aspect of the present invention, in the measuring system of the first aspect, the measuring device and the announcement device are driven by a battery provided on the announcement device side when the measuring device and the announcement device are combined. Therefore, a battery on the measuring device side is not required when the measuring device and the announcement device are combined.

According to a fifteenth aspect of the present invention, in the measuring system of the fourteenth aspect, the measuring device is combined with the announcement device with its cover for a battery storage part and a battery removed. Therefore, the presence or absence of the battery of the measuring device can be detected when the measuring device and the announcement device are combined, the battery will not be forgotten to be removed from the measuring device.

According to a sixteenth aspect of the present invention, in the measuring system of the fifteenth aspect, the cover for the battery storage part, which cover is provided in the measuring device, is shared as a cover for a battery storage part for storing a battery for the announcement device. Therefore, the cover for the battery storage part, which cover is removed from the measuring device, will not be lost when the measuring device and the announcement device are combined.

According to a seventeenth aspect of the present invention, in the measuring system of the fifteenth aspect, the cover for the battery storage part of the measuring device is provided with a combining means for combining the cover with the measuring device and a combination releasing means for removing the cover for the battery storage part from the measuring device. Therefore, the cover for the battery storage part will not be accidentally removed from the measuring device.

According to an eighteenth aspect of the present invention, in the measuring system of the fifteenth aspect, the announcement device is provided with a storage part for the battery removed from the measuring device. Therefore, loss of the battery of the measuring device and an accident due to its scatter can be prevented.

According to a nineteenth aspect of the present invention, in the measuring system of the sixteenth aspect, a tip shape of a rib provided on the inner wall of the cover for the battery storage part has a flat part and a circular part for pressing plural kinds of accessories. Therefore, even when batteries of different shapes are used between the measuring device and the announcement device, batteries of respective shapes can be held reliably.

According to a twentieth aspect of the present invention, in the measuring system of the first aspect, pattern lengths in a connector part for communication between the measuring device and the announcement device provided in the measuring device are different in a sliding direction of the measuring device when the measuring device is combined with the announcement device. Therefore, electrodes of the connector part can be connected in a desired order.

According to a twenty-first aspect of the present invention, in the measuring system of the first aspect, a terminal on the measuring device side for battery contact between the measuring device and the announcement device is formed at a portion of a main printed board of the measuring device. Therefore, easier assembly can be realized due to reduction in parts count and assembly man-hour of the measuring device.

According to a twenty-second aspect of the present invention, in the measuring system of the first aspect, a terminal on the measuring device side for electrically connecting the measuring device to the announcement device is provided in a battery storage part on the measuring device side. Therefore, a user can be prevented from improperly touching a terminal part when only the measuring device is used.

According to a twenty-third aspect of the present invention, in the measuring system of the first aspect, when measurement is not started while the measuring device is on standby for measurement, the announcement device promotes measurement start by voice or the like. Therefore, a measurement operator can be prevented from interrupting the operation halfway through the measurement procedure.

According to the twenty-fourth aspect of the present invention, in the measuring system of the first aspect, the remaining time is indicated by voice or the like by the announcement device during measurement by the measuring device. Therefore, a measurement operator can be easily informed of the elapsed time of the operation.

According to a twenty-fifth aspect of the present invention, in the measuring system of the first aspect, cutoff of power is informed by voice or the like by the announcement device when measurement by the measuring device is finished. Therefore, a measurement operator can be easily informed that power of the measuring device is cut off.

According to a twenty-sixth aspect of the present invention, in the measuring system of the first aspect, the initial setting of the measuring device such as a clock setting can be performed by an operating part on the announcement device side. Therefore, it is easy for an operator who needs the announcement device to perform time setting of the measuring device.

According to a twenty-seventh aspect of the present invention, in the measuring system of the first aspect, when the initial setting of the measuring device such as a clock setting is not performed when the announcement device and the measuring device are connected, the need for the initial setting is indicated by voice or the like by the announcement device. Therefore, an operator who needs the announcement device can be prevented from improperly performing measurement without performing time setting.

BRIEF DESCRIPTION OF THE DRAWINGS

FIG. 6 is a perspective view of a conventional measuring device.

FIG. 7 is a perspective view of the reverse face of the conventional measuring device.

DETAILED DESCRIPTION OF THE INVENTION

Hereinafter, a measuring system according to the present invention will be specifically described based on figures.

Figure 1:
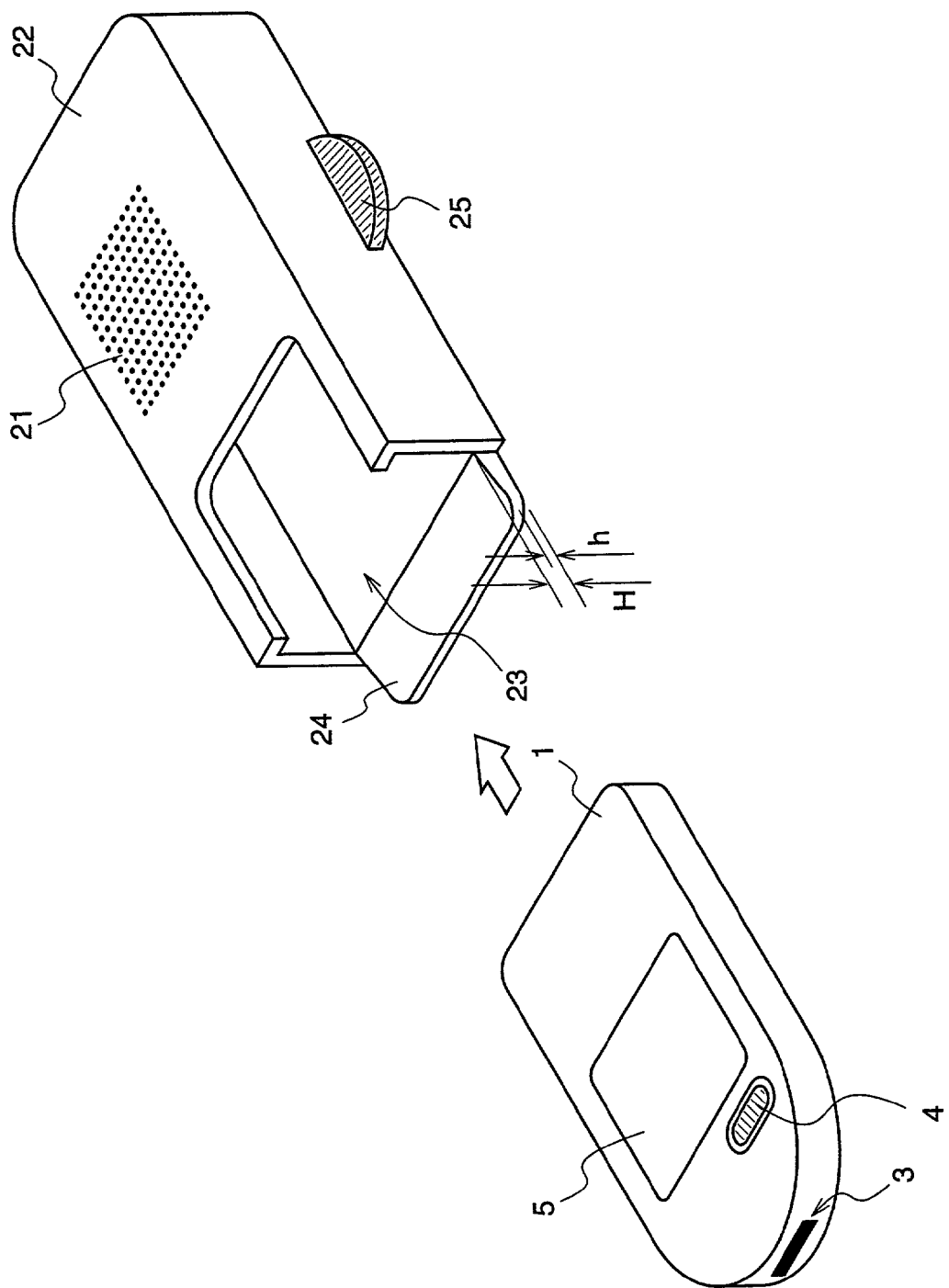
FIG. 1 is a perspective view of a measuring device and an announcement device constituting a measuring system according to the present invention.
Figure 2:
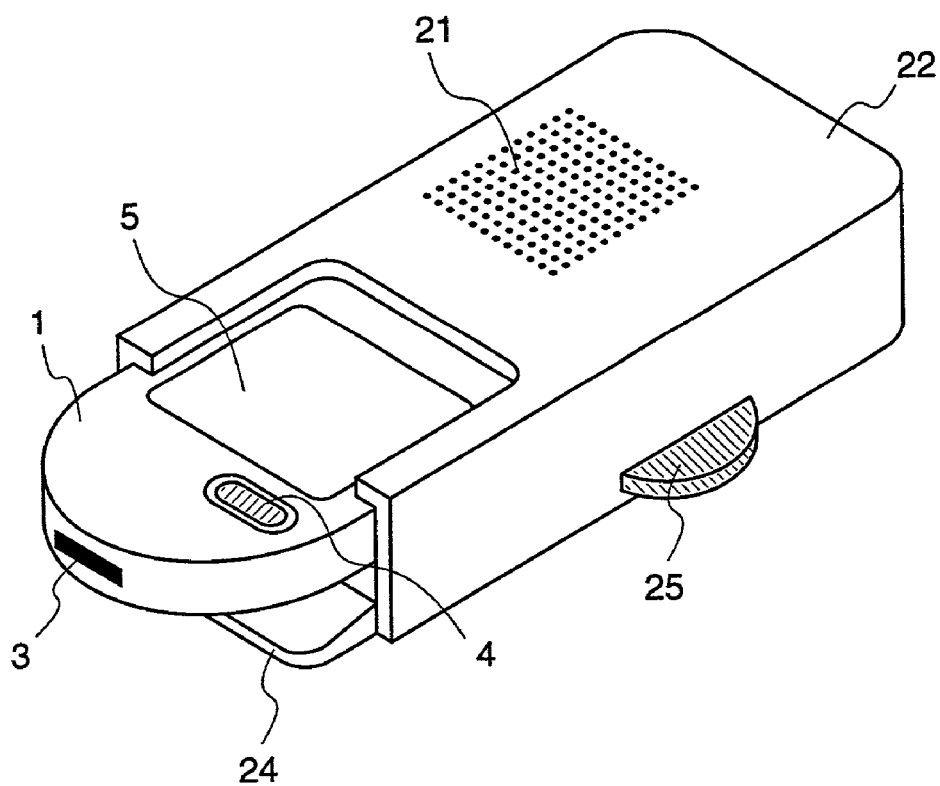
FIG. 2 is a perspective view of the measuring system according to the present invention.
Figure 3:
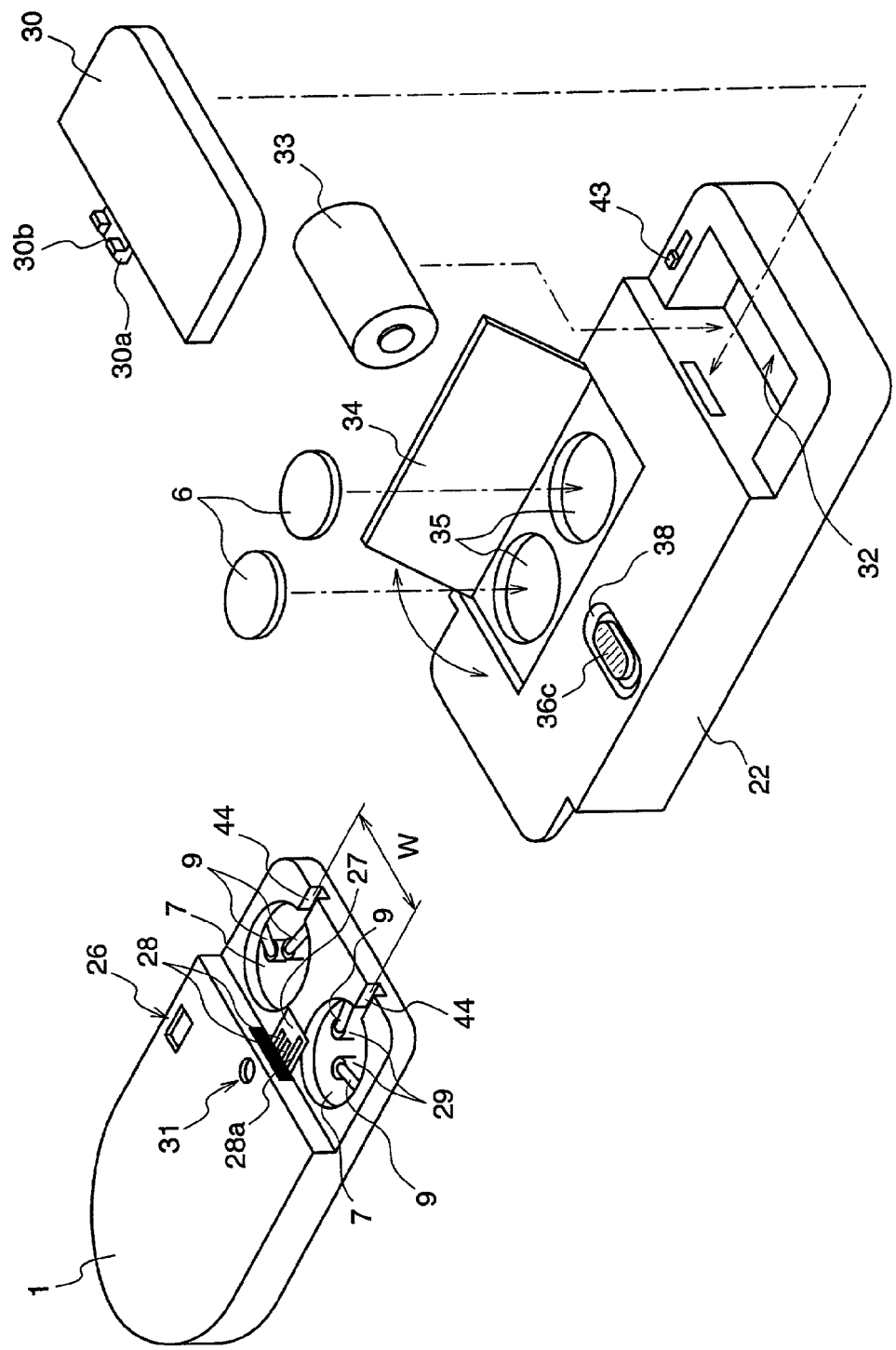
FIG. 3 is a perspective view of the measuring device and the announcement device constituting the measuring system according to the present invention, as seen from the base direction.

FIGS. 1 to 3 illustrate a measuring system according to the present invention. In the figures, the same reference numerals as those shown in FIGS. 6 and 7 denote the same or corresponding parts.

Figure 8:
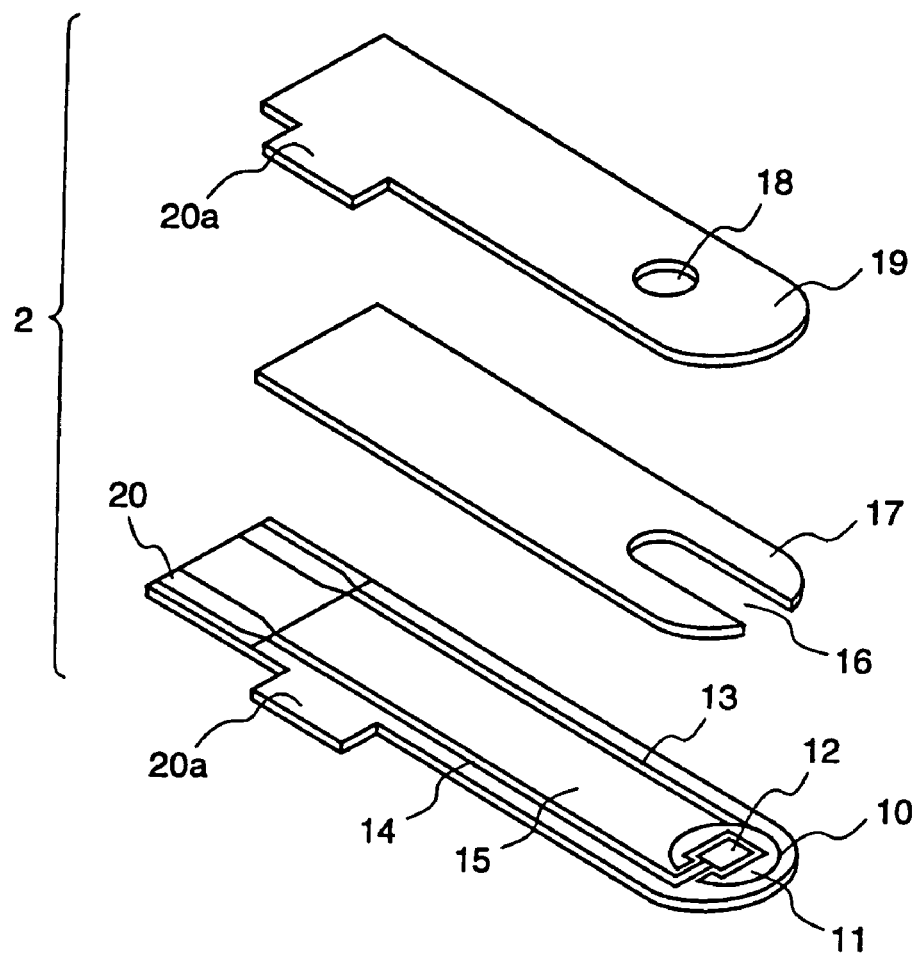
FIG. 8 is an exploded perspective view of a biosensor.
Figure 9:
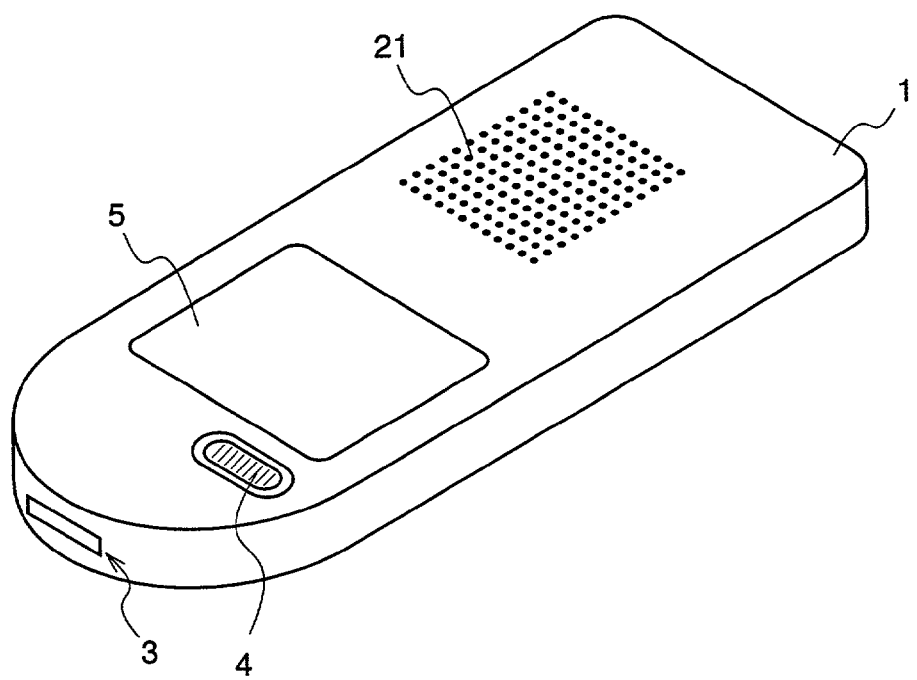
FIG. 9 is a perspective view of a conventional measuring device provided with a voice output function.

As shown in FIG. 1, a measuring device 1 is provided with a function of enabling measurement by itself, and a biosensor 2 (see FIG. 8) is inserted in a sensor insertion slot 3 and a prescribed operation is performed. Thus, information such as a measurement result is displayed on a display member 5. An optional device (announcement device) 22 can be combined with the measuring device 1, and can receive information such as a measurement result from the measuring device 1 or perform guidance of a measuring operation in a state of being combined with the measuring device 1 as shown in FIG. 2.

An opening 23 in which the measuring device 1 is inserted is provided in the front of the announcement device 22, and the opening 23 has a sloped part (guide) 24 which is formed so that the height H at the rear part is higher than the height h at the front part. An electronic circuit (communication unit) which generates a result obtained by communication with a communication unit (both of them not shown) of the measuring device 1 or provides guidance of a measuring operation with a voice is provided inside the announcement device 22, and the output is performed through a voice output part 21 on the top surface of the announcement device 22. The top surface of the announcement device 22 is shaped (recessed) so that the display member 5 of the measuring device 1 can be seen even after integration, and an operating part 25 is provided on the side of the announcement device 22.

A concave portion 26, a battery storage part 7, and a connector 27 for making electrical contact with the announcement device 22 are provided on the reverse (second) face of the measuring device 1 as shown in FIG. 3.

Inside the measuring device 1, is a measuring part comprising a converting means for converting an electrical resistance value of liquid to be examined (which liquid is obtained by the biosensor 2) to a characteristic value of the liquid to be examined, a storage means for storing the characteristic value, and a calculating means for performing various arithmetical operations such as an average value calculation based on a value stored in the storage means or the characteristic value obtained by measurement. A controller is provided for controlling the display member 5, and a main printed board (not shown) is provided with an electronic circuit such as a communicating means for communicating with the announcement device 22, and an electrode part (not shown). The connector 27 is formed at a portion of the main printed board in a united manner, and a pattern 28a for a ground connection is constructed to be longer than the other patterns.

A battery 33 is stored in a battery storage part 32 on the reverse (base-side) face of the announcement device 22. A change-over switch 43 for switching a language of a voice to be outputted is provided at a part which is covered with a back cover 30.

Figure 4:
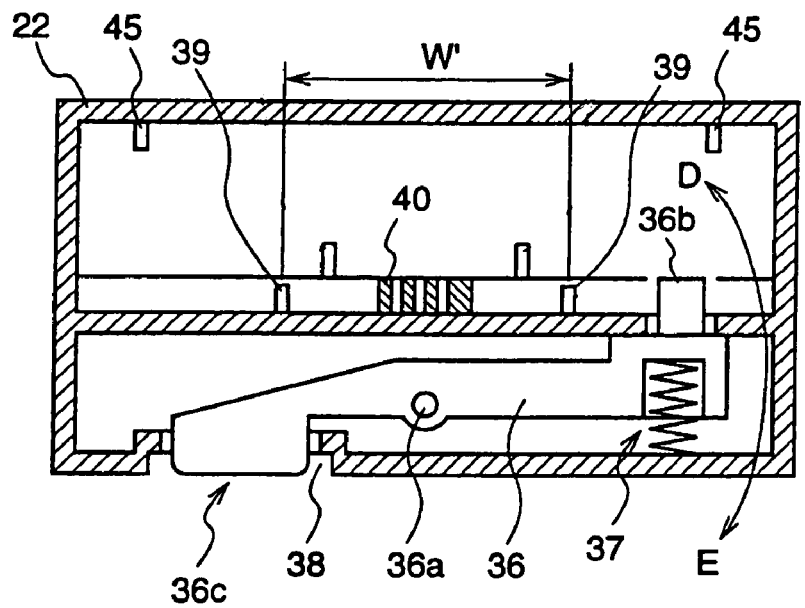
FIG. 4 is a sectional view of the announcement device according to the present invention.

FIG. 4 is a sectional view of the announcement device 22 as seen from the opening 23 side. Inside the announcement device 22, a lock lever 36 is held with a supporting point 36a as a center, and a lock part 36b is usually energized in the 'D' direction due to an action of a spring 37. A flat part 36c of lever 36 is provided on the opposite end of lever 36 with respect to the lock part 36b, with the supporting point 36a therebetween, and the flat part 36c is located inside a recessed portion 38 at the bottom of the announcement device 22. A reception part 40 for receiving the connector 27 of the measuring device 1 is provided in the inner part of the opening 23. A communicating means (not shown) for communicating with the measuring device 1 is provided inside the announcement device 22, and communication is performed through the connector 27 and the reception part 40. A distance regulation rib 45 for regulating the distance between the measuring device 1 and the reception part 40 side is provided on the internal top surface of the opening 23.

Figure 5:
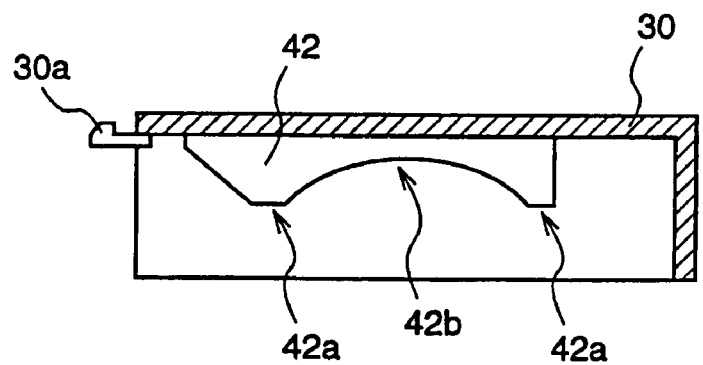
FIG. 5 is a sectional view of a battery storage part of the measuring device or the announcement device according to the present invention.

When the back cover 30 is attached to the measuring device 1, it is fixed to the measuring device 1 due to the action of a lock claw (engaging claw) 30a as shown in FIG. 5. While the battery 6 is pressed against the contact point 9 by a linear (straight) part 42a of a rib 42 at this time, contact pressure between the contact point 9 and the battery 6 is appropriately kept by a projection part 29 provided at the lower part of the contact point 9 so as to make contact with the contact point 9.

An operation of the measuring system having the above-described construction according to the present invention will be described.

When the measuring device 1 is integrated with the announcement device 22, a flat part (releasing part) 30b of the back cover 30 is pressed through an opening 31 in the measuring device 1 so that the lock claw 30a is released. The back cover 30 and the battery 6 are removed from the measuring device 1, and the measuring device 1 is inserted into the opening 23 of the announcement device 22. At this time, the measuring device 1 is guided into the inside of the announcement device 22 by the sloped part 24 of the announcement device 22. When the measuring device 1 is pushed further, grooves 44 spaced apart a groove width W in the measuring device 1 and guide ribs 39 spaced apart width W' equal to the above-mentioned width W in the announcement device 22 are engaged, so that the connector part 27 of the measuring device 1 is guided to the reception part 40 of the announcement device 22, the pattern 28a first makes contact with an electrode of the reception part 40 to establish a ground connection, and thereafter the rest patterns 28 are connected with the electrode.

After the connection between the connector 27 and the reception part 40 is completed, a lock part 36b of the lock lever 36 of the announcement device 22 and the concave (recessed) portion 26 on the base side of the measuring device 1 engage each other, thereby fixing the measuring device 1 to the announcement device 22.

In a state in which the measuring device 1 is locked in the announcement device 22, the flat part 36c of the lock lever 36 does not protrude from the base side of the announcement device 22 in the concave (recessed) portion 38 on the base of the announcement device 22, so that the lock lever 36 is not pressed and released improperly.

The back cover 30 removed from the measuring device 1 is attached to the announcement device 22 as a cover for the battery storage compartment 32 of the announcement device 22. At this time, the battery 33 is held by a curved part 42b of the rib 42 on the back cover 30. The battery 6 removed from the measuring device 1 is stored in a storage compartment 35 provided in the announcement device 22 at the same time, and enclosed with lid 34.

When being integrated, the measuring device 1 and the announcement device 22 are driven by the battery 33 in the announcement device 22.

In a state in which the measuring device 1 and the announcement device 22 are combined, the biosensor 2 is inserted in the sensor insertion slot 3 of the measuring device 1 to measure a sample. At this time, voice guidance for a measuring operation or a measurement result is outputted by voice from the voice output part 21. When measurement is not started while the measuring device 1 is on standby for measurement, the announcement device 22 promotes measurement start by voice or the like. The remaining time until a measurement result is outputted is indicated by voice or the like from the voice output means 21 of the announcement device 22 during measurement, whereby a measurement operator can be easily informed of the elapsed time of the operation. Cutoff of power is indicated when measurement is finished, whereby the elapsed time since a start of the measurement or the like is also indicated from the voice output part 21 of the announcement device 22.

By operating the operating part 25 of the announcement device 22, various setting operations such as volume setting of a voice to be outputted or setting of output repetition can be performed. Further, by operating the change-over switch 43, the language of the voice to be outputted can be switched.

The initial setting of the measuring device 1 such as clock setting can be performed arbitrarily by rotation and push operations of the operating part 25 on the announcement device 22, thereby correctly storing an acquisition date of a measurement value of measurement data or the like. When the initial setting of the measuring device 1 such as clock setting is not performed when the announcement device 22 and the measuring device 1 are connected with each other, the need for the initial setting is indicated from the voice output means 21, thereby preventing an operator who needs the announcement device 22 from improperly performing measurement without performing the time setting.

When an integration of the announcement device 22 and the measuring device 1 is released, the flat part 36c of the lock lever 36 in the announcement device 22 is pressed, so that the lock lever 36 is rotated (pivoted) in the direction of an arrow E with the supporting point 36a as a pivot, whereby the lock part 36b and the recessed portion 26 of the measuring device 1 are disengaged, and the measuring device 1 can be removed.

As described above, the measuring system according to the first embodiment of the present invention comprises a measuring device 1 which takes a substance to be measured and analyzes components of the substance to be measured, and an announcement device 22 which can generate voice or the like by being combined with the measuring device. The system is able to announce a measuring procedure or a measurement result in the measuring device 1 by voice by the announcement device 22, whereby even a weak-sighted person or those unfamiliar with handling of the device can measure accurately and recognize a measurement result.

The measuring device 1 and the announcement device 22 having a voice function can be integrated and separated, whereby, even when plural users require the voice function, only the measuring device 1 which manages measurement data has to be held by each person, and the announcement device 22 can be shared, resulting in reduction of the user's burden. Further, when the voice output part 21 has a breakdown, only the announcement device 22 has to be repaired and exchanged, and the measuring device 1 can be used continuously, thereby reducing inconvenience for a user.

The grooves 44 is provided in the measuring device 1, and the guide ribs 39 is provided on the announcement device 22 side. Thus, when a conventional measuring device or other models, for example, are to be combined with the announcement device 22, the guide ribs 39 serve as a stopper. Thus, a wrong insertion of the measuring device 1 can be prevented.

When the back cover 30 is not removed from the measuring device 1 at the integration of the measuring device 1 and the announcement device 22, the guide ribs 39 abut against the back cover 30, thereby preventing an irregular insertion of the measuring device 1. The same effect can be obtained also when the battery 6 is not removed from the measuring device 1, when the direction of the measuring device 1 is irregular, or when a measuring device which is not provided with the grooves 44 is to be inserted.

The back cover 30 of the measuring device 1 is removed to be attached to the battery storage compartment 32 of the announcement device 22 when the measuring device 1 and the announcement device 22 are integrated, thereby preventing loss of the back cover 30. At this time, the battery 6 removed from the measuring device 1 is stored in the battery storage compartment 35 of the announcement device 22, thereby preventing loss of the battery and an accident due to its scatter.

The flat part 30b of the back cover 30 is pressed from the opening 31 of the measuring device 1 so that a lock is released when the back cover 30 is removed from the measuring device. Thus, the back cover is not accidentally removed, resulting in prevention of an accident due to scatter of the battery.

The pattern for a ground connection is constructed to be longer than the other patterns in the connector 27 of the measuring device 1. Thus, when the measuring device 1 and the announcement device 22 are combined, the ground connection is initially established and connections of the rest of the patterns are completed thereafter, resulting in an electrically stable and reliable connection.

The connector 27 is formed at a portion of a main substrate of the measuring device 1 in a united manner (i.e., integrated), thereby realizing simplification of assembly processes due to reduction in parts count, assembly man-hour, and the like.

APPLICABILITY IN INDUSTRY

As described above, according to a measuring system of the present invention, even when plural users require a voice function, only a measuring device which manages measurement data has to be held by each person, and an announcement device can be shared, thereby reducing user's economical burden. Further, when a voice output part has a breakdown, only the announcement device has to be repaired and exchanged, and the measuring device can be used continuously, thereby enhancing convenience for a user.

The invention claimed is:
1. A measuring system comprising:
 a measuring device for receiving a substance to be measured, including:
  a measuring unit for quantitatively analyzing specific components of the substance to produce measurement results, and
  a display unit for visually displaying the measurement results; and
 an announcement device including a voice output unit for generating a voice when combined with said measuring device, said announcement device being detachably connected to said measuring device, and being operable to announce by voice at least one of a measuring procedure and the measurement results produced by said measuring unit of said measuring device.

2. The measuring system of claim 1, wherein said measuring device includes a communication unit for communicating information with said announcement device.

3. The measuring system of claim 1, wherein said announcement device includes a communication unit for communicating information with said measuring device.

4. The measuring system of claim 1, wherein said announcement device includes an operating part for operating said voice output unit.

5. The measuring system of claim 1, wherein said announcement device is operable to switch a language of the voice generated by said voice output unit.

6. The measuring system of claim 5, wherein said announcement device includes an operating lever for switching a language of the voice generated by said voice output unit, said operating lever being arranged so as to be covered by a casing of said announcement device.

7. The measuring system of claim 1, wherein said announcement device has an opening for receiving said measuring device, and has a outwardly-tapered slope at said opening.

8. The measuring system of claim 1, wherein each of said measuring device and said announcement device has an engagement mechanism for engaging each other when said measuring device and said announcement device are detachably connected.

9. The measuring system of claim 1, wherein said announcement device includes a lever for disengaging and disconnecting said measuring device from said announcement device, said lever being located on a base side of said announcement device.

10. The measuring system of claim 1, wherein said announcement device includes a locking part for engaging a recessed section of said measuring device to detachably connect said measuring device to said announcement device.

11. The measuring system of claim 1, wherein said measuring device is shaped so that only one end of said measuring device can be inserted into said announcement device to detachably connect said measuring device to said announcement device.

12. The measuring system of claim 1, wherein each of said measuring device and said announcement device has a mechanism for preventing improper insertion of said measuring device into said announcement device.

13. The measuring system of claim 1, wherein said announcement device has an inner wall with a rib for regulating the distance between said inner wall and said measuring device.

14. The measuring system of claim 1, wherein said announcement device has a battery storage compartment for housing a battery for driving said measuring device and said announcement device when said measuring device and said announcement device are detachably connected.

15. The measuring system of claim 14, wherein said measuring device includes a removable cover for covering a measuring device battery for driving only said measuring device, said measuring device and said announcement device being shaped and designed such that said removable cover and said measuring device battery must be removed to detachably connect said measuring device to said announcement device.

16. The measuring system of claim 15, wherein said removable cover is shaped and designed to cover said battery housed in said battery storage compartment of said announcement device when said measuring device is detachably connected to said announcement device.

17. The measuring system of claim 16, wherein said removable cover has an inner wall having a rib formed thereon, said rib having a flat part and a circular part for pressing plural kinds of accessories.

18. The measuring system of claim 15, wherein said removable cover has an engaging part for attaching said removable cover to said measuring device, and has a releasing part for releasing said removable cover from said measuring device.

19. The measuring system of claim 15, wherein said announcement device has a storage section for storing the measuring device battery removed from said measuring device.

20. The measuring system of claim 1, wherein said measuring device has a connector for communicating with said announcement device, said connector having pattern lengths different with respect to a sliding direction of said measuring device when said measuring device is detachably connected to said announcement device.

21. The measuring system of claim 1, wherein said measuring device includes a main printed board having a terminal for providing battery contact between said measuring device and said announcement device.

22. The measuring system of claim 1, wherein said measuring device has a battery storage compartment having a terminal for electrically connecting said measuring device to said announcement device.

23. The measuring system of claim 1, wherein said announcement device is operable to generate a voice to promote measurement start if a measurement process is not started when said measuring device is on standby for the measurement process.

24. The measuring system of claim 1, wherein said announcement device is operable to indicate a remaining amount of time by voice during a measurement process.

25. The measuring system of claim 1, wherein said announcement device is operable to indicate cutoff of power by voice when a measurement process is finished.

26. The measuring system of claim 1, wherein said announcement device includes an operating part for achieving an initial setting of said measuring device.

27. The measuring system of claim 1, wherein said announcement device is operable to indicate a need for an initial setting of said measuring device by voice, when the initial setting of said measuring device is not performed after said announcement device and said measuring device are detachably connected.

28. The measuring system of claim 1, wherein said measuring device and said announcement device are each shaped and designed such that, when said announcement device is combined with said announcement device, said display unit of said measuring device is exposed so as to allow a user to view the visually displayed measurement results.

* * * * *